United States Patent [19]

Bals et al.

[11] Patent Number: 5,060,529
[45] Date of Patent: Oct. 29, 1991

[54] APPARATUS FOR DETECTING GASEOUS CONSTITUENTS WITHIN THE INNER SPACE OF PACKAGES

[75] Inventors: Ion Bals, Cologny; Willy Hofer, Lully; Antoine Gagnebin, Geneva, all of Switzerland

[73] Assignee: Orbisphere Laboratories Neuchatel SA, Switzerland

[21] Appl. No.: 608,840

[22] Filed: Nov. 5, 1990

[30] Foreign Application Priority Data

Nov. 17, 1989 [CH] Switzerland ............... 4144/89

[51] Int. Cl.⁵ ............................................. G01N 1/10
[52] U.S. Cl. ................................................ 73/864.74
[58] Field of Search ........... 73/863.81, 863.83–863.85, 73/864.21–864.24, 864.74, 864.81, 864.83–864.87

[56] References Cited

U.S. PATENT DOCUMENTS

| | | | |
|---|---|---|---|
| 3,201,994 | 8/1965 | Adams | 73/864.74 |
| 3,374,678 | 3/1968 | McGuckin | 73/864.74 |
| 3,849,070 | 11/1974 | Garza et al. | 73/864.74 |
| 4,478,095 | 10/1984 | Bradley et al. | 73/864.21 |
| 4,791,821 | 12/1988 | Spencer | 73/864.74 |

Primary Examiner—Robert Raevis
Attorney, Agent, or Firm—Wigman & Cohen

[57] ABSTRACT

The gas detection apparatus comprises a holder for the temporary fixation of an associated package and which contains a contact surface. A hollow needle having a tip serves to penetrate a portion of the package which is freely exposed at the region of the contact surface. This hollow needle comprises at least two channels. An element serves for the essentially gas-tight connection of the hollow needle tip with the contact surface or the part of the package freely exposed therein. A component is connected by a connection line with one channel of the hollow needle. A suitable membrane-enclosed sensor, such as an amperometric sensor defining a sensor surface formed by a semi-permeable membrane, is preferably suspendingly arranged in the compartment. A preferably closable flushing or purging gas line communicates with the connection line and allows flushing the compartment, the connection line and the one channel. At least one liquid infeed line is flow-connected with the other channel of the hollow needle and allows for a preferably dosed introduction of displacement liquid into the internal space of the package to be pierced by the hollow needle. The compartment is provided with a liquid lock or trap device and contains a spatter protection layer or separation membrane which practically does not hinder the through-passage of gases and protects the sensor surface against deposition of liquids thereat.

13 Claims, 1 Drawing Sheet

APPARATUS FOR DETECTING GASEOUS CONSTITUENTS WITHIN THE INNER SPACE OF PACKAGES

BACKGROUND OF THE INVENTION

The present invention relates to an improved apparatus for detecting gaseous constituents such as, for instance, oxygen within the internal space or interior of gas-tight enclosed packages. In the context of this disclosure the term "packages" is employed in its broadest sense and encompasses, for instance, ampoules or vials, infusion or injection solution containers or receptacles, bottles and cans formed of, for instance, metal glass or plastic.

During the packing or unpacking of products, such as medicaments or treatment agents, foodstuffs, beverages, chemicals and various other types of materials, which are sensitive to certain gases, such as usually elementary oxygen, and therefor should not contain such gas or at most in a certain maximum quantity, and also for products, the packages of which should contain a certain gas, it is necessary to control by random sampling yet continually the properties of the gas phase contained in the internal space or interior of the package. This control operation is accomplished in order to continuously monitor possible deviations from set or reference values or some defects of the packaged material or product and/or the package or packaging installation.

Most of the previously commercially available equipment for accomplishing such type of control of the properties of the gas phase of already sealed or hermetically enclosed packages are either complicated in their usage, too expensive or operate with insufficient accuracy and consistency.

SUMMARY OF THE INVENTION

Therefore, with the foregoing in mind, it is a primary object of the present invention to provide a new and improved construction of apparatus for detecting gaseous constituents within the inner space of packages in a manner which is not afflicted with the aforenoted drawbacks or at least possesses such to a considerable lesser degree.

A further significant object of the present invention aims at the provision of an apparatus for detecting gaseous constituents within the interior of sealed packages in a highly reliable manner and without necessitating any complicated construction of such apparatus.

Still a further noteworthy object of the present invention is to provide an improved apparatus for detecting gaseous constituents in hermetically sealed packages during the packing or unpacking of various products.

Now, in order to implement these and still further objects of the invention, which will become more readily apparent as the description proceeds, the apparatus for detecting gaseous constituents within the internal space or interior of a sequence of normally gas-tight closed packages is manifested, among other things, by the features that there is provided a holder for the temporary fixation of a respective package. A hollow needle serves to puncture a portion of the package. This hollow needle contains at least two channels or ducts. A compartment or chamber is operatively connected with one channel or duct of the hollow needle. A sensor, such as an amperometric sensor, containing a sensor or detection surface is arranged within the compartment. There is also provided a device for the introduction of a displacement or flushing liquid into the internal space of the package which is pierced by the hollow needle.

A purging or flushing device serves to flush or scavenge the gas-conducting parts of the apparatus with an inert gas. Also arranged within the compartment is a spatter-protection layer or separation membrane which practically does not hinder the free passage of gases and protects the sensor or detection surface against the separation or deposition of liquids thereat.

BRIEF DESCRIPTION OF THE DRAWING

The present invention will now be described with reference to the single figure of the drawing which schematically illustrates a preferred exemplary of the inventive gas detecting apparatus.

DETAILED DESCRIPTION OF THE PREFERRED EMBODIMENTS

Figure 1:
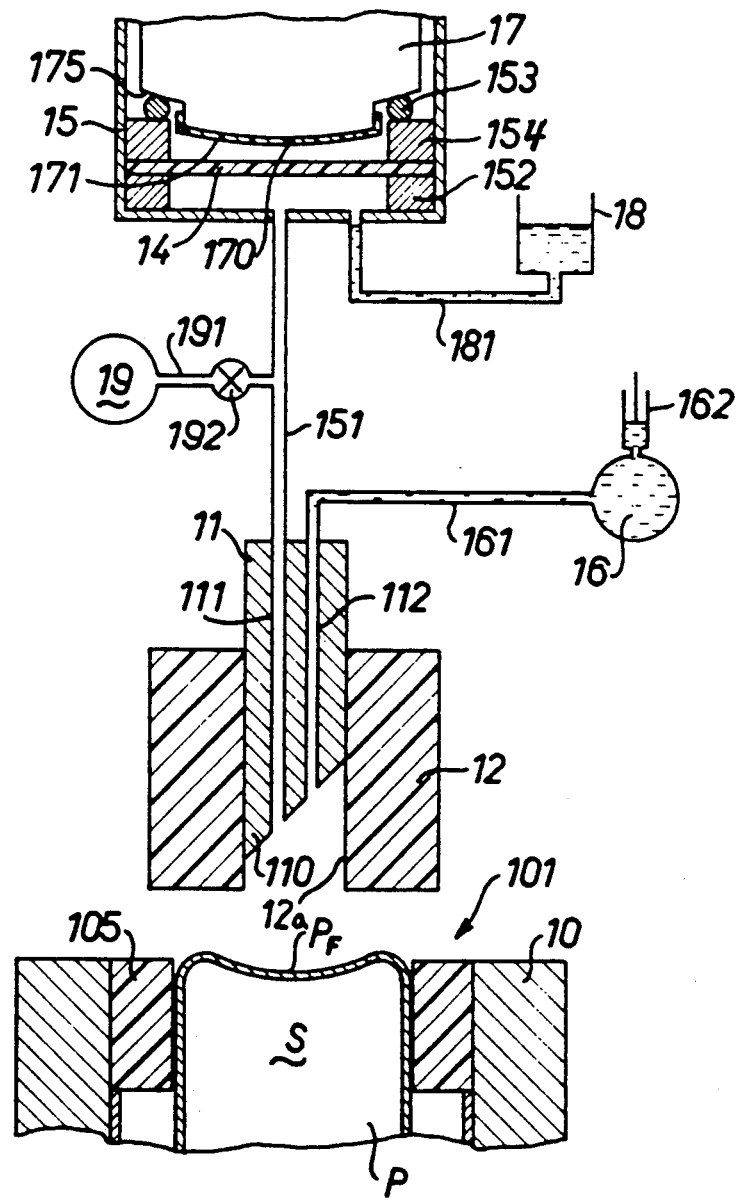

Describing now the single figure of the drawing, it is to be understood that only enough of the construction of the inventive gas detection apparatus has been illustrated therein as needed for one skilled in the art to readily understand the underlying principles and concepts of the present development.

It will be observed that a fragmentary illustrated package P, for instance an ampoule or vial, is temporarily fixed in a sample holder or holder member 10 which may be of, for instance, substantially cylindrical configuration. It should be understood that this holder or holder member 10 or a suitable fitting element which may be inserted therein has a configuration which appropriately corresponds to the shape or configuration of the package P which is to be tested. By way of example, the holder 10 generally can be constructed in the manner of a chuck which when appropriately rotated or threadably turned can be closed in order to receive and positionally fix the package P. In particular, the package P is fixed temporarily in the holder 10 such that there can be positively and simply accomplished the hereinafter described puncturing of a portion or part $P_F$ of the package P and which is preferably freely exposed in the holder 10.

By appropriately rotating or threadably turning the holder 10 in a reverse direction from that accomplished for positionally fixing the package P the latter, which as a general rule has been now destroyed, again can be released and the next package P can be positionally fixed in the sample holder 10 for undergoing a sequence of sample tests which are undertaken in conventional manner at the packages P.

The sample holder or holder member 10 preferably forms in conjunction with a rubber gasket or seal 105 and the freely exposed package portion $P_F$, here for instance the ampoule or vial base, a contact surface 101 upon which there can be mounted in practically fluid-tight fashion an element 12 formed of a preferably elastic material and having, for instance, a substantially ringshaped or cylindrical-shaped configuration.

The freely exposed portion or part $P_F$ of the package P, here constructed, by way of example, as an ampoule or vial and which is formed of glass, then can be scratched or scored by a hard metal pointed tool or equivalent means in order to define a fracture location which is formed at the package P upon penetration of the hollow needle 11.

This hollow needle contains a relatively sharp tip or puncture portion 110. Furthermore, as will be clearly seen by inspecting the drawing, this hollow needle 11 has at least two channels or ducts 111 and 112 which extend therethrough. As a general rule, the outer surface of the hollow needle 11 is substantially cylindrical and is sealingly inserted within the internal bore 12a of the element 12.

At the start of a sensing or detection cycle a small quantity of displacement or flushing liquid, for instance water, is delivered from a suitable source 16 through a liquid infeed line or conduit 161 which flow communicates with the channel or duct 112 and applied to the contact surface 101. in this way there can be prevented the penetration of ambient air into the internal space of the element 12 or, in other words, into the space which is not occupied by the hollow needle 11. The other channel or duct 111 of the hollow needle 11 is initially flushed or scavenged with an inert gas, for instance nitrogen, delivered from suitable source 19 via the flushing line or conduit 191 and the gas-conducting line 151. This inert gas does not influence the operation of a suitable sensor 17 arranged within a chamber 15 and which will be discussed more fully hereinafter. At the start and during the actual measurement operation the infeed of the scavenging or purging gas is interrupted by a valve 192 or equivalent structure which is usually automatically actuated.

Now, the freely exposed ampoule base or floor $P_F$ is pierced by the hollow needle or needle member 11, for instance in that this hollow needle 11 is lowered onto the holder 10 either by operation of a suitable motor drive or manually. This holder 10 is arranged at its base or lower end on any suitable support surface.

During such time as the element 12, which snugly bears against the contact surface 101, precludes entry of external or ambient air into the interior of the pierced ampoule or vial, a dosing or infeed device 162 infeeds a predetermined quantity of the previously mentioned displacement or flushing liquid, assumed here to be water, into the internal space S of the ampoule or vial and at that location displaces the same volume of gas. Typical volumes of displacement liquid lie in the range of 0.2 to 10 ml which, however,. also can be dependent upon the size of the gas space in the employed package P. For standard ampoules or vials displacement liquid quantities of only 0.5 are frequently sufficient.

The displaced gas arrives by means of the line or conduit 151 which is filled with the scavenging or purging gas into the compartment or chamber 15, which has only been shown in fragmentary illustration for simplification of the drawing. The aforementioned sensor 17 is inserted into this compartment or chamber 15. This sensor is typically a membrane-enclosed probe, notably an electroanalytical probe and preferably an amperometric probe or sensor. A particularly useful amperometric sensor is a Clark-type cell or electricode which possesses a semi-permeable membrane and is suitable for measuring The concentration of different electroavtice substances or gases. Such type of amperometric sensors have been described in detail in, for instance, U.S. Pat. No. 4,096,047, British Patent No. 2,415,298, European Pat. No. 0 043 611 or U.S. Pat. No. 4,518,477, the disclosures of which are incorporated herein in their entirety by reference.

For many fields of application of the invention there is preferred the use of a sensor for the determination of oxygen. Commercially available sensors of this type have, as a general rule, an approximately circular-shaped sensor surface which is arranged at its end face upon a substantially cylindrical body member. The compartment or chamber 15 for housing such sensor 17 then can be likewise of cylindrical or tubular shape and provided with a ringshaped annular shoulder 154 upon which bears a suitable gasket or sealing O-ring 153. An appropriate ring-shaped shoulder 175 of the sensor 17 bears against the sealing O-ring 153. A sensor membrane 170 is sealingly connected with the sensor 17 in conventional manner as taught, for instance, in the aforementioned patents.

During the course of investigation leading to the present invention, it has been found that a notable error source when employing Clark-type electrodes or cells in conjunction with media of mixed phase, such as fog or aerosols, is the formation of precipitation, condensation or spatters upon the outer surface of the membrane 170 which is exposed to the medium undergoing investigation. Preferably, and according to the invention, the detection or sensor surface of the amperometric sensor is arranged in so-to-speak "suspended" fashion, that is to say, practically as illustrated in the drawing with approximately horizontally disposed detection or sensor surface. Investigations have revealed that the measurement values of such sensors are quite appreciably affected or, in fact, destroyed by adhering material, for instance water droplets.

An essential feature for the successful, in other words, reliable, simple and continuous operation of the inventive gas detection apparatus resides in the provision of a spray or splatter protection layer or separating membrane 14 which covers the detect surface 171 of the membrane 170 of the sensor 17 and, as desired, could bear against such membrane 170 or be arranged in spaced relationship thereform.

Preferred spray protective layers or separation membranes 14 are constituted by gas-pervious layers or membranes having a flow resistance of less than 50%, especially less than 10%, which, however, are practically impervious for the liquid which is present. The impermeability for the liquid can be partially governed by the material of the spray protection layer of separation membrane 14 and completely or partially by the structure, especially the fine porosity. There are particularly preferred microporous layers or membranes formed of organic or inorganic materials such as, for instance, commercially available membrane- or layer-shaped materials having defined pore sizes in a range of about 0.1 μm to 1 μm and typically less than 0.5 μm. When using water as the displacement liquid, the splatter protective layer or separation membrane 14 is preferably decisively hydrophobic and formed of an organic polymer. A particular example of a separation membrane or spray protective layer having such properties are the commercially available microporous layers or membranes marketed under the trademark "GoreTex" by W. L. Gore, D-8011, Rutzbrunn, Germany. Such layers are, as a general rule, water-impervious below a certain pressure, for instance 2 bar, and have pore sizes of about 0.3 μm. Suitable layers have thicknesses of 100 μm up to 2 mm.

In order to render possible the through-passage of purging gas and displaced gas out of an examined package and to eliminate the rediffusion of ambient air, there is preferably used a lock or trap device 18, for instance a bubble counter or another container for the trap or blocking liquid, for instance water, which is connected in flow communication by means of a line or conduit 181 with the compartment or chamber 15.

It should be specifically understood that the gas detecting apparatus shown schematically in the single figure of the drawing only portrays the principles of a preferred embodiment of the invention and that, in particular, the actual measurement component, which normally would be arranged subsequent to the output of the fragmentarily illustrated sensor 17, need not be considered in any further detail because such measurement component br unit is well known and commercially available in different designs. It also should be understood that the lines or conduits 151, 161, 181 and 191 shown in the drawing could be of flexible design or possess flexible parts. Also, motor drives can be used, for instance, for the lowering and raising of the hollow needle 11 relative to the sample holder 10, for the actuation of the valve 191 for the scavenging or purging gas and for the actuation of the dosing or infeed device 162.

Furthermore, the inventive gas detection apparatus is not limited to detecting oxygen in the internal space of packages but can be employed in all other situations where certain threshold values of the absence or presence of electroactive gases should be reliably monitored within the internal space of packages or the like.

It also should be understood that the displacement or flushing liquid, here for instance water, introduces an electroactive gas which influences the measurement result, for instance oxygen, and, thus, the measurement values can be falsified. This error source is, however, as a general rule constant or can be maintained constant without any great difficulty and in any event can be compensated or corrected.

It is to be understood that the foregoing detailed description is given merely by way of illustration and that variations may be made therein without departing from the spirit of the invention.

What is claimed is:

1. An apparatus for detecting gaseous constituents within an inner space of each of a sequence of normally gas-tight sealed packages comprising:
   holder means for the temporary fixation of an associated package;
   a hollow needle for piercing a predetermined portion of the package;
   said hollow needle being provided with at least two channels;
   a compartment for receiving a sensor;
   a membrane-enclosed sensor arranged in said compartment;
   means for connecting said compartment with one channel of the hollow needle;
   said connecting means and said one channel of said hollow needle defining a gas-conducting portion;
   said membrane-enclosed sensor comprising a membrane defining a sensor surface arranged in said compartment;
   means for the introduction of a displacement liquid into the inner space of a package to be pierced by the hollow needle;
   means for flushing the gas-conducting portion with an inert gas defining a flushing gas;
   a separation membrane arranged in said compartment; and
   said separation membrane allowing the through-passage of gases practically without hindrance and protecting the sensor surface of the sensor against deposition of liquids thereat.

2. The apparatus as defined in claim 1, wherein said membrane-enclosed sensor comprises an amperometric sensor.

3. The apparatus as defined in claim 1, wherein said membrane-enclosed sensor comprises an amperometric oxygen detector defining a Clark-type cell.

4. The apparatus as defined in claim 1, further including means provided for said holder means for sealing, said sealing means and holder means forming a contact surface.

5. The apparatus as defined in claim 4, wherein said hollow needle comprises a tip for piercing a portion of the package which is freely exposed at the region of the contact surface.

6. The apparatus as defined in claim 5, further including an element for the substantially gas-tight connection of the tip of the hollow needle with the contact surface.

7. The apparatus as defined in claim 5, further including an element for the gas-tight connection of the tip of the hollow needle with the freely exposed portion of the package.

8. The apparatus as defined in claim 1, wherein said flushing means comprises a flushing gas line and closable valve means provided for said flushing gas line, said flushing gas line flow-communicating with the connection means between said one channel and said compartment means and enabling flushing of the compartment, the connection means and the one channel of the hollow needle.

9. The apparatus as defined in claim 1, wherein said means for introducing the displacement liquid comprises a liquid infeed line flow-communicating with another channel of said at least two channels of said hollow needle; and said displacement liquid introducing means further comprising a dosing device for the infeed of a predetermined quantity of displacement liquid.

10. The apparatus as defined in claim 1 further including trap means operatively connected with said compartment; and said trap means containing a liquid which allows the through-passage of the flushing gas and prevents the diffusion of ambient air into said compartment.

11. The apparatus as defined in claim 1, wherein said separation membrane has a predetermined flow flow resistance for gases but essentially prevents the through-flow of liquids under operating conditions encountered by the gas detection apparatus.

12. The apparatus as defined in claim 11, wherein said separation membrane comprises a microporous layer formed of a organic polymer and having pore openings in the range of 0.1 $\mu$m to 1 $\mu$m.

13. An apparatus for detecting gaseous constituents within an inner space of sealed packages, comprising:
   holder means for the temporary fixation of an associated package; means for piercing a predetermined portion of the package; compartment for receiving a sensor;
   a membrane-enclosed sensor arranged in said compartment; for connecting said compartment means with said piercing means;
   said membrane-enclosed sensor comprising a membrane having a detection surface arranged in said compartment means;
   means for the introduction of displacement liquid into the inner space of a package which is to be pierced by the piercing means;
   means for flushing the connecting means with a flushing gas; a separation membrane arranged in said compartment means; and
   said separation membrane allowing the through-passage of gases practically without hindrance and protecting the detection surface of the sensor against deposition of liquid thereat.

* * * * *

UNITED STATES PATENT AND TRADEMARK OFFICE
CERTIFICATE OF CORRECTION

PATENT NO. : 5,060,529

DATED : October 29, 1991

INVENTOR(S) : Ion Bals et al

It is certified that error appears in the above-identified patent and that said Letters Patent is hereby corrected as shown below:

Column 3, line 42, "however,." should be --however,--;

line 45, "0.5" should be --0.5 ml--;

line 57, "The" should be --the-- and "electroavtice" should be --electroactive--;

Column 5, line 9, "br" should be --or--.

Column 6, line 6, delete "means".

Column 6, line 2, "flow Flow" should be --low flow--.

Column 6, line 3, "organic polymer" should be --hydrophobic organic polymer--.

Signed and Sealed this

Ninth Day of March, 1993

Attest:

STEPHEN G. KUNIN

Attesting Officer

Acting Commissioner of Patents and Trademarks